United States Patent
De Lange et al.

(10) Patent No.: US 9,260,423 B2
(45) Date of Patent: Feb. 16, 2016

(54) PROCESS FOR THE PREPARATION OF A THIOPRECURSOR FOR STATINS

(71) Applicant: DSM Sinochem Pharmaceuticals Netherlands B.V., Delft (NL)

(72) Inventors: Ben De Lange, Echt (NL); Dennis Heemskerk, Echt (NL); Karin Henderika Maria Bessembinder, Echt (NL)

(73) Assignee: DSM SINOCHEM PHARMACEUTICALS NETHERLANDS B.V., Delft (NL)

( * ) Notice: Subject to any disclaimer, the term of this patent is extended or adjusted under 35 U.S.C. 154(b) by 0 days.

(21) Appl. No.: 14/363,986

(22) PCT Filed: Dec. 6, 2012

(86) PCT No.: PCT/EP2012/074689
§ 371 (c)(1),
(2) Date: Jun. 9, 2014

(87) PCT Pub. No.: WO2013/083719
PCT Pub. Date: Jun. 13, 2013

(65) Prior Publication Data
US 2014/0343292 A1    Nov. 20, 2014

(30) Foreign Application Priority Data
Dec. 9, 2011   (EP) .................................... 11192749

(51) Int. Cl.
*C07D 405/12* (2006.01)
*C07D 417/12* (2006.01)
*C07D 319/06* (2006.01)

(52) U.S. Cl.
CPC ............ *C07D 417/12* (2013.01); *C07D 319/06* (2013.01); *C07D 405/12* (2013.01)

(58) Field of Classification Search
None
See application file for complete search history.

(56) References Cited

FOREIGN PATENT DOCUMENTS

WO     WO 02/06266      1/2002
WO     WO 02/098854    12/2002

OTHER PUBLICATIONS

International Search Report for PCT/EP2012/074689 mailed Jan. 4, 2013.

*Primary Examiner* — Laura L. Stockton
(74) *Attorney, Agent, or Firm* — Nixon & Vanderhye P.C.

(57) ABSTRACT

The present invention relates to a process for the preparation of a precursor for the synthesis of hexanoic acid derived statins and to the use of said precursor in the manufacture of a medicament.

5 Claims, No Drawings

PROCESS FOR THE PREPARATION OF A THIOPRECURSOR FOR STATINS

This application is the U.S. national phase of International Application No. PCT/EP2012/074689, filed 6 Dec. 2012, which designated the U.S. and claims priority to EP Application No. 11192749.7, filed 9 December 2011.

FIELD OF THE INVENTION

The present invention relates to a process for the preparation of a precursor for the synthesis of hexanoic acid derived statins and to the use of said precursor in the manufacture of a medicament.

BACKGROUND OF THE INVENTION

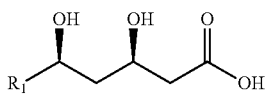
(1)

Hexanoic acid derived statins of general formula (1) or salts thereof inhibit the enzyme 3-hydroxy-3-methylglutaryl-coenzyme A reductase (HMG-CoA reductase) and are thus useful as a hypolipidemic and hypocholesterolemic agents. Examples of these statins are cerivastatin wherein $R_1$ is a radical of formula (C), fluvastatin wherein $R_1$ is a radical of formula (F), pitavastatin wherein $R_1$ is a radical of formula (P) and rosuvastatin wherein $R_1$ is a radical of formula (R).

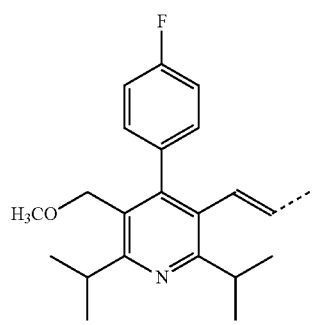
(C)

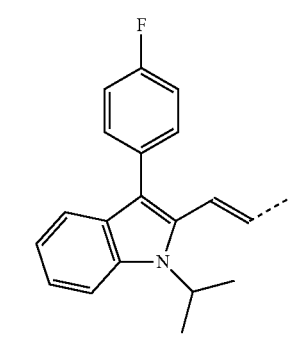
(F)

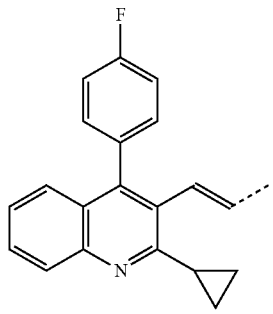
(P)

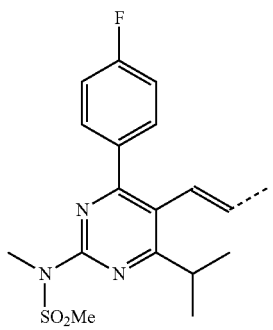
(R)

For the introduction of the chiral part of the abovementioned molecules, intermediates of general formula (2) play a pivotal role.

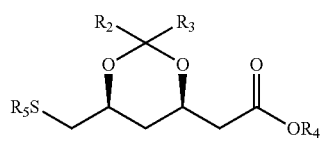
(2)

In the compounds of general formula (2) $R_2$ and $R_3$ each independently stand for an alkyl with for instance 1 to 12 carbon atoms and $R_2$ and $R_3$ may form a ring together with the carbon atom to which they are bound. The group $R_4$ is a carboxylic acid protecting group. For preparative purposes, $R_4$ must be a group that can be easily removed after formation of the statin structure. Suitable groups in this respect have proven to be sec-butyl, tert-butyl, iso-propyl and the like. $R_5$ is an aryl group that is suitable for a one-pot or modified Julia-Kocienski olefination, examples of which are tetrazole-based groups and substituted phenyl and benzimidazole type compounds (e.g. P. R. Blakemore, J. Chem. Soc., Perkin Trans. 1, 2002, 2563). For the purpose of this olefination the compound of general formula (2) is oxidized to the sulfone of general formula (3).

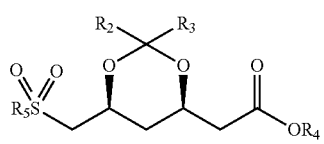
(3)

A method for preparing chiral diol sulfones is described in WO 2002/098854 and WO 2001/096311. In these citations, a sulfone is prepared from an alcohol, more in particular tert-butyl 2-((4R,6S)-6-(hydroxymethyl)-2,2-dimethyl-1,3-dioxan-4-yl)acetate known as "Kaneka alcohol". The preparation of such an alcohol is described in EP 1024139. The synthesis in the prior art has several disadvantages, the most prominent being that many reaction steps are required and that trifluoromethanesulfonic anhydride or another sulfonic acid derived activating agent is used to activate the alcohol function to an extent that a nucleophilic attack with a thiol is possible. Trifluoromethanesulfonic anhydride is an extremely hazardous and expensive component, which causes costly work-up procedures due to environmentally problematic waste streams. It is an object of the present invention to provide a process, in which not only the use of an activating agent like trifluoromethanesulfonic anhydride is omitted but which also reduces the number of chemical conversions required.

DETAILED DESCRIPTION OF THE INVENTION

In a first aspect of the invention, there is provided a method for the preparation of a compound of general formula (2)

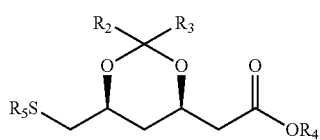

(2)

comprising contacting, in the presence of water, a compound of general formula (4)

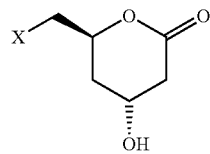

(4)

with an alcohol of general formula $R_4$—OH, a thiol of general formula $R_5$—SH and an acetalization agent.

In the context of the present invention X refers to a halogen atom such as bromine, chlorine, fluorine or iodine, preferably bromine or chlorine. $R_2$ and $R_3$ each independently stand for an alkyl with for instance 1 to 12 carbon atoms, preferably 1 to 6 carbon atoms, an alkenyl with for instance 1 to 12 carbon atoms, preferably 1 to 6 carbon atoms, a cycloalkyl with for instance 3 to 7 carbon atoms, a cycloalkenyl with for instance 3 to 7 carbon atoms, an aryl with for instance 6 to 10 carbon atoms or an aralkyl with for instance 7 to 12 carbon atoms, each of $R_2$ and $R_3$ may be substituted and wherein $R_2$ and $R_3$ may form a ring together with the carbon atom to which they are bound. The groups $R_2$ and $R_3$ are for example halogens or hydrocarbon groups with for instance 1 to 10 carbon atoms, optionally containing one or more heteroatoms, for instance Si, N, P, O, S, F, Cl, Br or I. In practice, $R_2=R_3$ is methyl is most preferred. In the compound of general formula (2) $R_4$ is an alkyl or alkenyl group with 1 to 6 carbon atoms. Such relatively small substituents are favorable since they have a high so-called 'carbon economy', i.e. the use of organic material is lower than is the case with more complex protecting groups. Suitable examples are allyl, iso-butenyl, n-butyl, sec-butyl, tert-butyl, ethyl, methyl, 2-methyl-3-pentyl, 4-methyl-1-pentyl, 4-methyl-2-pentyl, n-propyl, iso-propyl or vinyl. The alcohol $R_4$—OH may be added in stoichiometric amounts but also larger amounts and the alcohol $R_4$—OH may even be present as solvent. In the compound of general formula (2), $R_5$ is an aryl group that for instance is suitable for a one-pot or modified Julia-Kocienski olefination. Suitable aryl groups are e.g. described in P. R. Blakemore, J. Chem. Soc., Perkin Trans. 1, 2002, 2563. Preferred aryl groups include tetrazole, substituted phenyl and benzimidazole type compounds. Specific examples of preferred aryl groups include, pyridine-2-yl, pyrimidin-2-yl, benzothiazol-2-yl, 1-methyl-1H-tetrazol-5-yl, 1-phenyl-1H-tetrazol-5-yl, 1-tert-butyl-1-H-tetrazol-5-yl, 3,5-bis(trifluoromethyl)phenyl-1-yl, 1-methylimidazol-2-yl, benzimidazol-2-yl, 4-methyl-1,2,4-triazol-3-yl and iso-quinolin-1-yl. Most preferred aryl groups are 1-methyl-1H-tetrazol-5-yl, 1-phenyl-1H-tetrazol-5-yl, 1-tert-butyl-1-H-tetrazol-5-yl, benzothiazol-2-yl, and 3,5-bis(trifluoromethyl)phenyl-1-yl.

The method is carried out in the presence of a base such as an alkanolate like the methanolate, ethanolate, propanolate or butanolate of an alkaline metal. Examples are potassium tert-butanolate, potassium ethanolate, sodium methanolate and the like. Preferably the thiol of general formula $R_5$—SH and the base are mixed prior to addition of said mixture to the compound of general formula (4) and the alcohol $R_4$—OH. Following admixture of the abovementioned components the method further comprises addition of an acetalization agent. The acetalization agent is an acetal, an alkoxy-alkene or a ketone. Suitable examples of acetalization agents are acetone, cyclohexanone, cyclopentanone, dimethoxypropane, 2-ethoxypropene, 2-methoxypropene and 3-pentanone.

The reaction with the alcohol $R_4$—OH and the acetalization agent preferably is carried out in the presence of an acid such as an inorganic or organic acid. Suitable acids are acetic acid, formic acid, hydrobromic acid, hydrochloric acid, methanesulphonic acid, sulfuric acid, p-toluenesulphonic acid and the like. In addition, the reaction with the alcohol $R_4$—OH and the acetalization agent preferably is carried out in the absence of water. Water may be removed before, during or after the addition of the alcohol $R_4$—OH and/or the acetalization agent. Removal of water may be carried out using various methodologies known to the skilled person such as evaporation or distillation, optionally under reduced pressure, addition of drying agents such as anhydrous salts, molecular sieves and the like, phase separation or combinations thereof. In a preferred embodiment the method of the present invention is carried out in the presence of a solvent capable of forming an azeotrope with water, preferred examples of which are acetonitrile, allyl alcohol, iso-amyl acetate, n-amyl alcohol, n-butyl acetate, iso-butyl acetate, n-butyl alcohol, sec-butyl alcohol, iso-butyl propionate, iso-butyronitril, ethyl butyrate, ethyl alcohol, 2-heptanone, 3-heptanone, 4-heptanone, n-hexyl alcohol, 2-pentanol, n-propyl alcohol, iso-propyl alcohol, toluene. In summary, the method of the present invention comprises the steps of:
  (a) mixing a compound of general formula $R_5$—SH with a base;
  (b) adding to the mixture obtained in step (a) water and a compound of general formula (4);
  (c) adding during and/or following step (b) an alcohol of general formula $R_4$—OH;
  (d) adding an acetalization agent and removal of water and removing water prior to, during or after said adding
  (e) adding an acid to the mixture obtained in step (c) and/or step (d)

The method of the first aspect of the invention may be carried out at temperatures ranging from −20° C. to 150° C., preferably ranging from 0° C. to 100° C., more preferably ranging from 10° C. to 70° C. Suitable reaction times are from 10 min to 48 h, preferably from 30 min to 24 h, more preferably from 1 h to 18 h.

In one embodiment, the compound of general formula (2) is isolated. This may be achieved by addition of water or an aqueous solution and optional neutralization by means of addition of a base such as carbonates, hydrogen carbonates, hydroxides and the like. The organic phase of the mixture thus obtained may be separated from the aqueous phase and optionally further purified by washing with water or an aqueous solution. Final isolation of the compound of general formula (2) from the organic phase is achieved by crystallization, precipitation, evaporation of the organic phase or combinations thereof. The resulting compound of general formula (2) may optionally be re-crystallized or purified by distillation.

The starting material of general formula (4) may be prepared according to procedures known to the skilled person, such as for instance described in EP 1404844. The method of the first aspect of the invention has the advantage that a variety of groups $R_4$ can be introduced in a single step without the need to perform multiple steps such as first preparing the methyl ester, hydrolyzing said methyl ester and introducing an alternate ester group. Such additional steps have the disadvantage of reducing overall yield, introducing unwanted impurities and/or reducing optical purity through racemization. Consequently the products of general formula (2) obtained by the method of the present invention are isolated in unprecedented high yields and are of high purity.

In a second aspect of the invention there is disclosed the use of a compound of general formula (2) obtained according to the first aspect of the invention in the manufacture of an antilipemic medicament. Suitably, the compound of general formula (2) is converted into a statin of formula (1) with $R_1$ is a radical of formula (A), (C), (F), (P) or (R) as defined above.

In a first embodiment of the second aspect, the compound of general formula (2) is oxidized in manners known in the art, for example by oxidation with hydrogen peroxide or other oxidants like peracids (e.g. 3-chloroperoxybenzoic acid, peroxyacetic acid, monoperoxyphthalic acid), bleach, tert-BuOCl, perborates, N-oxides, permanganate, chromate, chlorate, bromate, perchlorate, periodate, tert-butyl hydroperoxide, oxone, peroxodisulfates and air/oxygen. If necessary, the oxidation can be carried out in the presence of an appropriate catalyst, such as salts or oxides of the metals V, Ce, Mn, Ni, Fe, Cu, Os, Mo, W, Re, or Ru or organic catalysts like iso-butyraldehyde in the case of air/oxygen or tetramethylpiperidine N-oxide (TEMPO) in the case of bleach. The resulting sulfones are of general formula (3) with $R_2$, $R_3$, $R_4$, and $R_5$ as defined above. The oxidation generally is performed in a solvent, such as dichloromethane, chloroform, 1,2-dichloroethane, methanol, ethanol, 2-propanol, acetonitrile, acetic acid, toluene, water, NMP, DMSO, DMF, tetrahydrofuran (THF), or MTBE. It is also possible to use biphasic solvent systems consisting of an aqueous phase and an organic phase in the presence of a phase-transfer catalyst, like quaternary ammonium salt or quarterly phosphonium salt (like tetraalkylammonium halide, e.g. tetrabutylammonium bromide) or crown ether (like 18-crown-6). Another class of suitable solvents comprises ionic liquids like, for example, 1,3-dialkyl imidazolium salts or N-alkyl pyridinium salts of acids like hexafluorophosphoric acid or tetrafluoroboric acid or trifluoromethane sulfonic acid, or with $(CF_3SO_2)_2N^-$ as anionic counterpart. Generally, a reaction temperature of about −20° C. or higher is effective. Preferably, a temperature of about 0° C. or higher is applied, more preferably a temperature close to ambient temperature (18-25° C. i.e. around 20° C.). A temperature of about 150° C. or lower generally is effective to bring about the oxidation. Generally, the reaction temperature will be about 100° C. or lower, more preferably about 60° C. or lower, most preferably about 40° C. or lower. The molar amount of oxidant to thio-ether generally is about 1 to 1 or higher, preferably about 2 to 1 or higher, more preferably about 3 to 1 or higher. Generally, the amount of terminal oxidant to thio-ether will be about 20 to 1 or lower, preferably about 10 to 1 or lower, most preferably about 5 to 1 or lower. The sulfone of general formula (3) can be isolated by aqueous extraction of excess oxidant/catalyst and subsequent removal of the solvent by evaporation. If water-miscible solvents like alcohols or aprotic polar solvents are applied as reaction medium, the reaction mixture can be partitioned between an aqueous and an organic phase prior to this operation, in order to extract the solvent to the aqueous phase. If ionic liquids are applied as reaction medium, the sulfone can be isolated by extraction with an organic solvent immiscible with the ionic liquid, followed by evaporation of the solvent. Alternatively, the sulfone of general formula (3) can be isolated from the reaction mixture by precipitation or crystallization, e.g. by addition of (or solvent switch to) an anti-solvent like hexane, heptane, iso-octane, or water. If desired, further purification can be performed by chromatography or re-crystallization.

In a second embodiment, the sulfone of general formula (3) is treated with an aldehyde $R_6$—CH=O, in which $R_6$ is chosen so as to obtain suitable precursors to useful statin-type compounds including cerivastatin, fluvastatin, pitavastatin and rosuvastatin or in which $R_6$ is a suitable precursor to these moieties (cf. WO 2002/098854 and WO 2001/096311). Preferred examples of aldehyde $R_6$—CH=O are 4-(4-fluorophenyl)-2,6-diisopropyl-5-(methoxymethyl)nicotinaldehyde, 3-(4-fluorophenyl)-1-isopropyl-1H-indole-2-carbaldehyde, 2-cyclopropyl-4-(4-fluorophenyl)quinoline-3-carbaldehyde and N-(4-(4-fluorophenyl)-5-formyl-6-isopropylpyrimidin-2-yl)-N-methylmethanesulfonamide as these aldehydes are the precursors for cerivastatin, fluvastatin, pitavastatin and rosuvastatin, respectively. This reaction preferably is carried out in the presence of a base, preferred examples of which are lithium hydride, potassium hydride, sodium hydride, lithium hexamethyldisilazane, sodium hexamethyldisilazane, potassium hexamethyldisilazane, solid potassium hydroxide, solid sodium hydroxide, metal alkoxides, such as sodium methoxide, lithium methoxide and potassium methoxide, lithium tert-butoxide, potassium tert-butoxide, sodium tert-butoxide, lithium bis-trimethylsilylamide, sodium bis-trimethylsilylamide, potassium bis-trimethylsilylamide, sodium amide, P4-tBu and 1,8-diazabicyclo [5.4.0]undec-7-ene and the like.

In a third embodiment, following the Julia-Kocienski olefination, the resulting product (5) may be isolated and purified after which it is de-protected to give hexanoic acid derived statins of general formula (1) wherein $R_1$ is a radical of formula (C), (F), (P) or (R) or salts thereof. Alternatively, deprotection may be carried out without isolation and/or purification of intermediate product (5). Deprotection is carried out according to procedures known to the skilled person, for instance by using acid such as hydrochloric acid as described in U.S. Pat. No. 6,844,437 or WO 2007/000121.

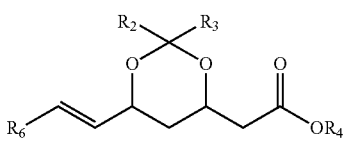

(5)

EXAMPLES

Example 1

2-((4R,6S)-6-((Benzo[6]thiazole-2-ylthio)methyl)-2,2-dimethyl-1,3-dioxan-4-yl)acetic acid methyl ester 2-Mercapto-1H-benzothiazole (33.4 g, 200 mmol) was added to 28.8 g of NaOH-32% and 22.0 g of water. Then (4R,6S)-6-(chloromethyl)-4-hydroxytetrahydropyran-2-one (EP 1404844, 32.9 g, 200 mmol) was added in 1 h at 25-30° C., keeping the pH between 12-12.5 by addition of NaOH-32%. The reaction mixture was stirred at 20-25° C. for 2h. Then 200 mL of methanol was added and the pH adjusted with concentrated aqueous HCl to 0.7-0.8. The reaction was stirred for 20 h and the pH adjusted to −0.5 with concentrated aqueous HCl. Then methanol/water was removed by distillation under vacuum to give thick oil. To this oil 200 mL of methanol was added, stirred for 1 h and concentrated again. Then 150 mL of methanol was added. The precipitated salts were removed by filtration. The methanol was removed again by distillation under vacuum. Next 320 mL of toluene and 200 mL of 5% aqueous NaCl was added to the residue. The organic layer was separated and about 75 mL removed by distillation. To the clear solution was added methanesulphonic acid (0.96 g, 10 mmol) and 2,2-dimethoxy propane (31.2 g, 300 mmol). The mixture was stirred for approximately 20 h at 20-25° C. Then 200 mL of 0.5 N aqueous NaOH was added. The phases were stirred, separated and the organic phase washed with water (1×100 mL). After concentration of the organic phase, the title compound was obtained as yellow oil (55.9 g, yield 76%). $^1$H NMR (300 MHz, CDCl$_3$) δ 8.22 (d, 1H), 8.01 (d, 1H), 7.64-7.58 (m, 2H), 4.62-4.52 (m, 1H), 4.35-4.25 (m, 1H), 3.86 (dd, 1H), 3.67 (s, 3H), 3.42 (dd, 1H), 2.43 (dd, 2H), 1.70 (dt, 1H), 1.37-1.26 (m, 1H), 1.35 (s, 3H), 0.79 (s, 3H).

Tentative Example 2

2-((4R,6S)-2,2-Dimethyl-6-((1-methyl-1H-tetrazol-5-ylthio)methyl)-1,3-dioxan-4-yl) acetic acid methyl ester 1-Methyl-1H-tetrazole-5-thiol (5-mercapto-1-methyltetrazole, 23.3 g, 200 mmol) was added to 28.8 g of NaOH-32% and 22.0 g of water. Then (4R,6S)-6-(chloromethyl)-4-hydroxytetrahydropyran-2-one (EP 1404844, 32.9 g, 200 mmol) was added in 1 h at 25-30° C., keeping the pH between 12-12.5 by addition of NaOH-32%. The reaction mixture was stirred at 20-25° C. for 2 h. Then 200 mL of methanol was added and the pH adjusted with concentrated aqueous HCl to 0.7-0.8. The reaction was stirred for 20 h and the pH adjusted to −0.5 with concentrated aqueous HCl. Then methanol/water was removed by distillation under vacuum to give thick oil. To this oil 200 mL of methanol was added, stirred for 1 h and concentrated again. Then 150 mL of methanol was added. The precipitated salts were removed by filtration. The methanol was removed again by distillation under vacuum. Next 320 mL of toluene and 200 mL of 5% aqueous NaCl was added to the residue. The organic layer was separated and about 75 mL removed by distillation. To the clear solution was added methanesulphonic acid (0.96 g, 10 mmol) and 2,2-dimethoxy propane (31.2 g, 300 mmol). The mixture was stirred for approximately 20 h at 20-25° C. Then 200 mL of 0.5 N aqueous NaOH was added. The phases were stirred, separated and the organic phase washed with water (1×100 mL). After concentration of the organic phase, the title compound was obtained as a liquid. $^1$H NMR (300 MHz, CDCl$_3$) δ 4.40-4.22 (m, 2H), 3.92 (s, 3H), 3.68 (s, 3H), 3.40 (dd, 2H), 2.48 (dd, 2H), 1.74 (dt, 1H), 1.42 (s, 3H), 1.39-1.29 (m, 1H), 1.35 (s, 3H).

Example 3

2-((4R,6S)-6-((benzo[d]thiazol-2-ylsulfonyl)methyl)-2,2-dimethyl-1,3-dioxan-4-yl)acetic acid methyl ester 2-(4R,6S)-6-((Benzo[d]thiazole-2-ylthio)methyl)-2,2-dimethyl-1,3-dioxan-4-yl)acetic acid methyl ester (60.0 g, 163 mmol) was dissolved in methanol (200 mL) and Na$_2$WO$_4$.2H$_2$O (5.34 g, 16.2 mmol, 10 mol %) was added, followed by 40 mL of methanol for rinsing. Next 60 mL of a 30% H$_2$O$_2$ solution (580 mmol) was added in 2 h keeping the temperature below 25° C. and the pH at about 6.0 with aqueous 4M NaOH (in total 2.2 mL required). After the addition was completed, the mixture was stirred for 18 h at 20° C., then 3h at 40° C. and cooled again to 20° C. The precipitated solid was isolated by filtration and washed with 50 mL of methanol. After drying the title compound was obtained as a white solid (49.8 g, yield 76%). $^1$H NMR (300 MHz, CDCl$_3$) δ 8.22 (d, 1H), 8.01 (d, 1H), 7.64-7.58 (m, 2H), 4.65-4.55 (m, 1H), 4.41-4.28 (m, 1H), 3.86 (dd, 1H), 3.67 (s, 3H), 3.42 (dd, 1H), 2.45 (dd, 2H), 1.70 (dt, 1H), 1.38-1.32 (m, 1H), 1.35 (s, 3H), 0.79 (s, 3H).

Example 4

2-((4R,6S)-6-((1-methyl-1H-tetrazol-5-ylsulfonyl)methyl)-2,2-dimethyl-1,3-dioxan-4-yl)acetate methyl ester 2-((4R,6S)-2,2-Dimethyl-6-((1-methyl-1H-tetrazol-5-ylsulfonyl)methyl)-1,3-dioxan-4-yl) acetic acid methyl ester (31.6 g, 100 mmol) was dissolved in methanol (150 mL) and Na$_2$WO$_4$.2H$_2$O (3.0 g, 10 mol %) was added. The temperature was increased to 40-45° C. Then 32 mL of a 30% H$_2$O$_2$ solution (310 mmol) was added in 2 h at 40-45° C. When the addition was completed, the mixture was stirred for 2.5 h at 40-45° C. and again 30 mL of 30% H$_2$O$_2$ was added in 2 h. When the addition was completed, the reaction mixture was cooled to 20-25° C. and left stirring for 18 h. The precipitated solid was isolated by filtration and washed with 50 mL of methanol. After drying the title compound was obtained as a white solid (29.1 g, yield 83%). $^1$H NMR (300 MHz, CDCl$_3$) δ 4.58-4.50 (m, 1H), 4.38-4.28 (m, 1H) 4.32 (s, 3H), 3.82 (dd, 1H), 3.68 (s, 3H), 3.56 (dd, 1H), 2.45 (ddd, 2H), 1.69 (dt, 1H), 1.42-1.31 (m, 1H), 1.38 (s, 3H), 1.00 (s, 3H).

Example 5

Preparation of 2-((4R,6S)-6-((E)-2-(4-(4-fluorophenyl)-6-isopropyl-2-(N-methylmethylsulfonamido)pyrimidin-5-yl)vinyl)-2,2-dimethyl-1,3-dioxan-4-yl)acetate, methyl ester N-(4-(4-fluorophenyl)-5-formyl-6-isopropylpyrimidin-2-yl)-N-methylmethanesulfonamide (1.0 g, 2.9 mmol) and 2-((4R,6S)-6-((1-methyl-1H-tetrazol-5-ylsulfonyl)methyl)-2,2-dimethyl-1,3-dioxan-4-yl) acetate methyl ester (0.79 g, 2.3 mmol) were added to tetrahydrofuran (10 mL). The mixture was heated until all reactants were dissolved and then cooled to −60° C. At this temperature 3.3 mL of a NaHMDS solution (1 M in tetrahydrofuran, total 3.3 mmol) was added in 1 h while keeping the temperature between −50 and −60° C. When dosing was completed, the temperature was allowed to increase to −10° C. after which the reaction was quenched with 10% aqueous NH$_4$Cl (10 mL). The phases were separated and the organic phase was washed successively with 10% aqueous NH$_4$Cl (1×10 ml) and 10% aqueous Na$_2$CO$_3$ (3×10 mL). The organic phase was evaporated to give the title compound as a solid (0.58 g, 1.1 mmol, 48% yield). $^1$H NMR (300 MHz, CDCl$_3$) δ 7.66 (dd, 2H), 7.09 (t, 2H), 6.53 (d, 1H), 5.49 (dd, 1H), 4.42-4.21 (m, 2H), 3.72 (s, 3H), 3.58 (s, 3H), 3.52 (s, 3H), 3.49-3.32 (m, 1H), 2.54 (ddd, 2H), 1.59-1.43 (m, 2H), 1.50 (s, 3H), 1.41 (s, 3H), 1.28, (dd, 6H).

The invention claimed is:

1. A method for the preparation of a compound of formula (2):

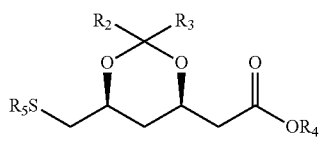

(2)

wherein R$_2$ and R$_3$ each may be substituted and independently stand for an alkyl group with 1 to 12 carbon atoms, an alkenyl group with 2 to 12 carbon atoms, a cycloalkyl group with 3 to 7 carbon atoms, a cycloalkenyl group with 3 to 7 carbon atoms, an aryl group with 6 to 10 carbon atoms, an aralkyl group with 7 to 12 carbon atoms, or together form a ring with the carbon atom to which they are bound, and wherein R$_4$ is an alkyl group with 1 to 6 carbon atoms or alkenyl group with 2 to 6 carbon atoms, and wherein R$_5$ is an aryl group, the method comprising the steps of:
(a) mixing a compound of formula R$_5$—SH with a base;
(b) adding to the mixture obtained in step (a) water and a compound of formula (4):

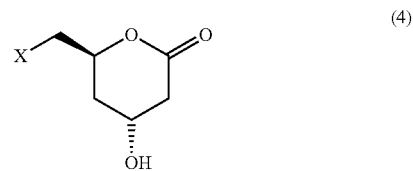

(4)

wherein X is halogen;
(c) adding during and/or following step (b) an alcohol of formula R$_4$—OH;
(d) adding an acetal or an alkoxy-alkene or a ketone and removing water prior to, during or after said adding; and
(e) adding an acid to the mixture obtained in step (c) and/or step (d).

2. The method according to claim 1, wherein R$_4$ is selected from the group consisting of allyl, iso-butenyl, n-butyl, sec-butyl, tert-butyl, ethyl, methyl, 2-methyl-3-pentyl, 4-methyl-1-pentyl, 4-methyl-2-pentyl, n-propyl, iso-propyl and vinyl.

3. The method according to claim 2, wherein said acetal is dimethoxypropane, said alkoxy-alkene is 2-ethoxypropene or 2-methoxypropene, and said ketone is acetone, cyclohexanone, cyclopentanone or 3-pentanone.

4. The method according to claim 3 wherein said compound of formula R$_5$—SH is selected from the group consisting of benzimidazol-2-thiol, 3,5-bis(trifluoromethyl)thiophenol, 1-tert-butyl-1-H-tetrazol-5-thiol, 2-mercapto-1H-benzothiazole, 1-methylimidazole-2-thiol, 1-methyl-1H-tetrazole-5-thiol, 4-methyl-1,2,4-triazol-3-thiol, 1-phenyl-1H-tetrazole-5-thiol, pyridine-2-thiol, pyrimidine-2-thiol and iso-quinolin-1-thiol.

5. The method according to claim 4 wherein X is bromine or chlorine, and each of R$_2$ and R$_3$ is methyl.

* * * * *